United States Patent [19]

Clark

[11] Patent Number: 4,542,027

[45] Date of Patent: Sep. 17, 1985

[54] LAIDLOMYCIN PHENYLCARBAMATE

[75] Inventor: Robin D. Clark, Palo Alto, Calif.

[73] Assignee: Syntex (U.S.A.) Inc., Palo Alto, Calif.

[21] Appl. No.: 582,691

[22] Filed: Feb. 23, 1984

[51] Int. Cl.[4] .................. A61K 31/35; C07D 309/10
[52] U.S. Cl. ................................... 514/459; 549/343
[58] Field of Search ..................... 549/343; 424/283

[56] References Cited

U.S. PATENT DOCUMENTS 3,794,732  2/1974  Raun ................................. 424/283
4,431,665  2/1984  Kluge et al. ....................... 424/283

Primary Examiner—Nicky Chan
Attorney, Agent, or Firm—Grant D. Green; Tom M. Moran; Alan M. Krubiner

[57] ABSTRACT

A compound represented by the formula

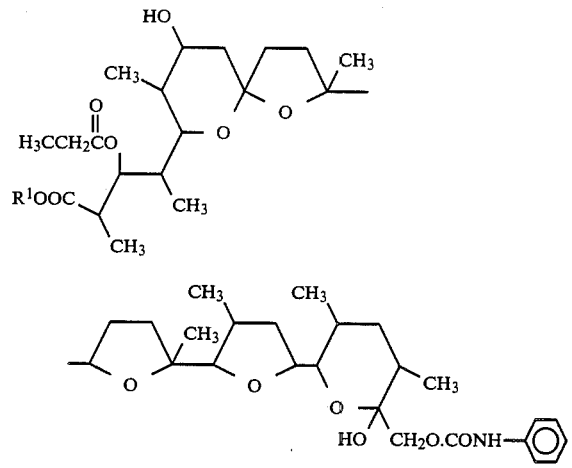

wherein $R^1$ is an alkali metal cation or hydrogen and which useful for increasing the feed efficiency of ruminants and for treating coccidiosis in domestic animals, especially chickens.

7 Claims, No Drawings

LAIDLOMYCIN PHENYLCARBAMATE

BACKGROUND OF THE INVENTION

1. Field of the Invention

This invention relates to a novel derivative of laidlomycin which is useful for increasing the feed efficiency in ruminants and treating coccidiosis in domestic animals, especially in chickens.

The antibiotic laidlomycin is a known compound which inhibits the growth of Gram positive bacteria. See the Journal of Antibiotics, Vol. XXIX, No. 7, pp. 759–761, July, (1976) and Vol. XXVII, No. 11, pp. 884–888, Nov., 1974. The aliphatic and alicyclic hydrocarbon acyl esters of the alcohol at carbon 26 are set out in U.S. Pat. No. 4,431,663. Monensin is also a known antibiotic and has been shown to be useful in increasing feed utilization in ruminants. See for example, U.S. Pat. No. 3,794,732. Carbamate derivatives of monensin are set out in U.S. Pat. No. 4,294,925.

As discussed in the above-mentioned U.S. Pat. No. 3,794,732, it is important to increase the efficiency of feed utilization in domestic animals, especially meat-producing and milk-producing animals such as cattle. Carbohydrates form a large part of these animals' diets, and the efficiency of carbohydrate utilization is desirably increased by treatment which encourages intraruminal production of propionate rather than acetate from carbohydrates. The theory behind this phenomena is discussed in the U.S. Pat. No. 3,799,732 patent.

The improved efficiency of feed utilization resulting from the use of laidlomycin phenylcarbamate can be determined by observing an increased concentration or molar percentage of propionate in the rumen. In addition, laidlomycin phenylcarbamate suppresses rumen lactic acid production, thereby assisting in the prevention or treatment of bloat in ruminant animals.

Propionate production enhancement and lactic acid suppression is surprisingly and unexpectedly high for laidlomycin phenylcarbamate. Laidlomycin phenylcarbamate has been found to be a highly stable laidlomycin derivative in solution and feed premixes, particularly in comparison with laidlomycin acylates. A third salutory characteristic is that the presence of the phenylcarbamate group renders the laidlomycin moiety subject to assay by conventional analytical means such as UV spectral analysis.

SUMMARY OF THE INVENTION

One aspect of this invention is a compound represented by the formula

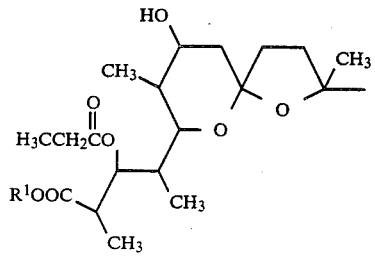

(A)

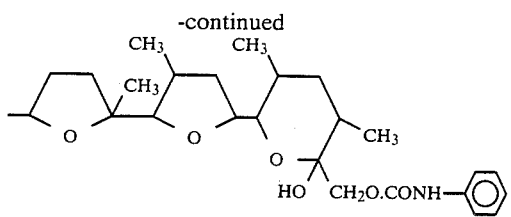

wherein $R^1$ is hydrogen or an alkali metal cation (e.g. sodium, potassium or lithium).

Another aspect of the invention is the combination of one of these compounds with a suitable feed carrier for a ruminant animal. A further aspect of the invention is a process for increasing the efficiency of feed utilization of an animal having a functional rumen (a ruminant) which comprises orally administering to such animal a feed efficiency increasing amount of at least one compound represented by formula (A).

Still another aspect of this invention is a method for preventing coccidial infections in a bird or animal host having need for such prevention, which comprises administering an anticoccidially effective amount of a compound of formula (A).

Still another aspect of this invention is a veterinary composition which comprises at least one compound represented by formula (A) and a veterinary pharmaceutically acceptable excipient.

FURTHER DISCUSSION AND DESCRIPTION OF PREFERRED EMBODIMENTS

The compounds of this invention include those compounds of formula (A) where $R^1$ is hydrogen or an alkali metal salt. The phenyl carbamate is derived from a phenyl isocyanate.

The carbamate is readily prepared by treating laidlomycin, or an alkali metal salt thereof, with phenyl isocyanate at a temperature between 25°–150° C. for a period of 10–60 minutes. The reaction is carried out in a suitable inert solvent such as a halogenated alkane or the like.

Preferably the phenyl carbamate will be prepared by adding an equimolar amount of phenyl isocyanate to laidlomycin predissolved in a solvent such as pyridine. The solution is then heated at about 70° C. for approximately 30 minutes. The resulting laidlomycin phenylcarbamate is then recovered by conventional extraction and separatory means.

Administration of a compound of this invention results in improved feed utilization and protects against lactic acid acidosis. The causative mechanism of ketosis is a deficient production of propionate compounds. A presently recommended treatment is administration of propionic acid or feeds which preferentially produce propionate. Because the compounds of this invention encourage propionate production from ordinary foods, feed efficiency is increased and the incidence of ketosis is reduced.

The compounds of this invention are most readily administered orally. The easiest way to administer the compounds is merely by mixing them with a suitable feed carrier. However, the compounds can be usefully administered in other ways. For example, they can be combined with a suitable, non-toxic veterinary pharmaceutical excipient incorporated into tablets, drenches, boluses or capsules and dosed to the animals. Formulation of the compounds of this invention in such dosage forms can be accomplished by means or methods well known in the veterinary pharmaceutical art. Each individual dosage unit should contain a quantity of the compound which has a direct relation to the proper daily dose for the animal to be treated.

Capsules are readily produced by filling gelatin capsules with any desired form of the desired compound alone or diluted with a pharmaceutical excipient such as an inert powdered diluent, e.g. sugar, starch or purified crystalline cellulose in order to increase its volume for convenience in filling capsules.

Tablets of the compounds of this invention are made by conventional pharmaceutical processes. Manufacture of tablets is a well known and highly advanced art. In addition to the active ingredient, a tablet usually contains other pharmaceutical excipients such as a base, a disintegrator, an absorbant, a binder, and a lubricant. Typical bases include lactose, fine icing sugar, sodium chloride, starch and mannitol. Starch is also a good disintegrator as is alginic acid. Surface active agents such as sodium lauryl sulfate and dioctyl sodium sulfosuccinate are also used. Commonly used absorbants again include starch and lactose while magnesium carbonate is also useful for oily substances. Frequently used binders are gelatin, gums, starch, dextrin and various cellulose derivatives. Among the commonly used lubricants are magnesium stearate, paraffin wax, various metallic soaps and polyethylene glycol.

The method of the invention can also be practiced by the administration of the compound as a slow release bolus. Such boluses are made as tablets are made except that a means to delay the dissolution of the compound is provided. Boluses are made to release for lengthy periods. The slow dissolution is assisted by choosing a highly water-insoluble form of the compound. A substance such as iron filings is added to raise the density of the bolus and keep it static on the bottom of the rumen.

Dissolution of the compound is delayed by use of a matrix of insoluble materials in which the drug is embedded. For example, substances such as vegetable waxes, purified mineral waxes, and water-insoluble polymeric materials are useful.

Drenches of the compounds are prepared most easily by choosing a water-soluble form of the compound. If an insoluble form is desired for some reason, a suspension may be made. Alternatively, a drench may be formulated as a solution in a physiologically acceptable solvent such as polyethylene glycol.

Suspensions of insoluble forms of the compounds can be prepared in non-solvents such as vegetable oils such as peanut, corn, or sesame oil; in a glycol such as propylene glycol or a polyethylene glycol; or in water, depending on the form of the compound chosen.

Suitable physiologically-acceptable adjuvants are necessary in order to keep the compound suspended. The adjuvants can be chosen from among the thickeners, such as carboxymethylcellulose, polyvinylpyrrolidone, gelatin, and the alginates. Many classes of surfactants serve to suspend the compounds of this invention. For example, lecithin, alkylphenol polyethylene oxide adducts, naphthalenesulfonates, alkylbenzenesulfonates, and the polyoxyethylene sorbitan esters are useful for making suspensions in liquid non-solvents.

In addition many substances which effect the hydrophilicity, density, and surface tension of the liquid can assist in making suspension in individual cases. For example, silicone anti-foams, glycols, sorbitol, and sugars can be useful suspending agents.

The suspendable compounds may be offered to the grower as a suspension, or as a dry mixture of the compounds and adjuvants to be diluted before use.

These compounds may also be administered in the drinking water of the ruminants. Incorporation into drinking water is performed by adding a water-soluble or water-suspendable form of the desired antibiotic to the water in the proper amount. Formulation of the compound for addition to drinking water follows the same principles as formulation of drenches.

The most practical way to treat animals with the compounds of the invention is by the formulation of the compound into the feed supply. Any type of feed may be medicated with the compounds, including common dry feeds, liquid feeds, and pelleted feeds.

The methods of formulating drugs into animal feeds are well known. It is usual to make a concentrated drug premix as a raw material for medicated feeds. For example, typical drug premixed may contain from about 1 to about 400 grams of drug per pound of premix. The wide range results from the wide range of concentration of drug which may be desired in the final feed. Premixes may be either liquid or solid.

Generally the compounds' daily dosage will be about 0.1 to 1.0 mg per kg body weight, preferably about 0.3 to 0.8 mg/kg. Thus, an 800 pound (about 360 kg) steer would receive about 36 to 360 mg and preferably about 109 to 290 mg.

The formulation of ruminant feeds containing the proper amount of the compounds for useful treatment is mainly a matter of arithmetic. It is necessary only to calculate the amount of compound which it is desired to administered to each animal, to take into account the amount of feed per day which the animal eats and the concentration of compound in the premix to be used, and calculate the proper concentration of compound in the feed.

All of the methods of formulating, mixing, and pelleting feeds which are normally used in the ruminant feed art are entirely appropriate for manufacturing feeds containing the compounds of the method.

The compounds of this invention are also effective in preventing coccidial infections in warm blooded animal hosts. The animals in which these compounds are useful include ruminants such as cattle, sheep, and goats as well as non-ruminants such as horses, pigs, chickens and particularly young chicks. The means of administration is similar to that for the treatment of ruminants and preferably is given orally, particularly to young chicks in their feed. The dosages useful for treating coccidial infections are from 0.1 to 3.0 mg/kg.

The following examples set forth methods for preparing representative compounds of this invention and biological data for representative compounds of this invention. It is understood, of course, that the examples are not to be read as limiting the scope of the claimed subject matter, but are given by way of illustration of the preparation and use of the invention.

EXAMPLE 1

A. Crude laidlomycin (4.8 grams) was chromatographed on silica gel using ethyl acetate as the eluant. Elution with 1.0 liter of ethyl acetate and collecting the 400–700 ml fractions affords a solution of sodium laidlomycin in ethyl acetate. Removing the ethyl acetate under vacuum afforded sodium laidlomycin (2.2 grams) having a melting point of 259°–261° C., with an Rf of 0.5 using ethyl acetate.

Preparation of Laidlomycin Phenylcarbamate

Phenyl isocyanate (2.38 g, 20 mmol) was added to a solution of laidlomycin (14 g, 20 mmol) in 100 ml of pyridine. The mixture was heated in an oil bath at 70° for 30 min. The mixture was cooled, diluted with dichloromethane, washed with 5% aqueous hydrochloric acid and water, and evaporated. The residue was purified by silica gel chromatography (75% ether hexane, 0.01% formic acid eluent) to afford 10 g of laidlomycin phenylcarbamate as an amorphous solid which melted at 88°–90° C. Carbon-13 NMR spectroscopy confirmed the structure.

EXAMPLE 2

BIOLOGICAL ACTIVITY

Two separate fermentation models were used to evaluate effects of laidlomycin and laidlomycin phenylcarbamate upon volatile fatty acids (VFA) and lactic acid production. Test compounds were solubilized in absolute ethanol at concentrations of 1 mg/ml and were serially diluted twofold in absolute ethanol through six additional concentrations. Aliquots of 200 μl were transferred to 18×150 mm test tubes, which were used as incubation vessels, and the ethanol was evaporated.

For both fermentation models rumen fluid from a rumen-fistulated steer, consuming a 100% alfalfa hay diet, was obtained before the morning feeding. The fluid was strained through four layers of cheesecloth, mixed with an equal volume of $CO_2$-saturated buffer, and 10 ml was transferred to each of the incubation vessels. All tubes were fitted with gas-release stoppers under an atmosphere of $CO_2$ and were incubated in a shaking waterbath at 39° C. Buffer used in the incubations for VFA production (table 1) contained a total of 80 mmol of hexose equivalents/liter from a variety of carbohydrate substrates and was buffered at a normal intraruminal pH that typically decreased from pH 6.8 to not less than pH 6.4 by the termination of incubation. This medium, designed to be microbiologically nonselective, encouraged VFA production with no accumulation of lactic acid. Buffer used to study lactic acid accumulation (table 1) contained 150 mmol of glucose/liter and had little buffering capacity. This medium favored growth of lactic acid-producing bacteria and allowed rapid production of lactic acid coupled with a precipitous drop in pH from pH 6.2 to less than pH 5 during the course of an incubation.

Fermentation was terminated at 9 h for the VFA fermentations and at 5.5 h for the lactic acid fermentations by addition of 2 ml of 25% metaphosphoric acid to the incubation tubes. Aliquots were frozen overnight, thawed, centrifuged at 30,000 × g for 10 min and the resulting supernatants analyzed for either L(+)-lactic acid or VFA. The L(+)-lactic acid was analyzed via a specific enzymatic assay in which the concentration of lactic acid in the fermentation broth was quantified by the increase in absorbance of light at 340 nm when nicotinamide adenine dinucleotide was reduced by lactic acid with the aid of L(+)-lactic dehydrogenase. VFA were analyzed via gas chromatography using a Varian chromatograph equipped with a flame ionization detector. Acids were separated on a glass column (0.64×182.9 cm) packed with 10% SP-1200/1% $H_3PO_4$ on Chromosorb-WAW ®, 80–100 mesh. This column was obtained pre-packed from Supelco, Inc., Bellefont, Pennsylvania. Chromatographic conditions included a column temperature of 145° C., an injector temperature of 190° C., a detector temperature of 190° C., a carrier gas flow of 45 ml/min and an injection volume of 1 μl.

Net production rates of all acids were calculated by subtracting the concentration of acids in the incubation fluid before incubation from the concentration determined in each tube after incubation. Molar proportions of acetic, propionic, and butyric acids produced were calculated by dividing the production rate of individual acids by the sum of the production rates of the three acids. Data were analyzed by analysis of variance (SAS, 1979). Comparisons (Duncan's multiple range test) of individual means were made when treatment effects ($P<0.05$) were indicated.

Results of testing (Tables 2 and 3) clearly demonstrated a superiority of laidlomycin phenylcarbamate relative to laidlomycin as an enhancer of propionic acid production and an inhibitor of lactic acid production. Laidlomycin increased propionic acid production to 108% and 109% of control when it was added to the incubation media at 10 and 20 μg/ml, respectively (Table 2). However, laidlomycin phenylcarbamate caused a 108 to 110% increase in propionic acid production when it was present at less than 1 μg/ml of incubation contents. Furthermore, with 20 μg/ml of laidlomycin phenylcarbamate, propionic acid production was increased to more than 130% of control. Statistical analysis over all concentrations of this ionophore indicated that laidlomycin phenylcarbamate was more potent than laidlomycin ($P<0.05$).

Laidlomycin caused lactic acid production to be reduced to only 81% of control even when it was added at the high concentration of 20 μg/ml (table 3). However, laidlomycin phenylcarbamate reduced lactic acid production to 21% of control, respectively, when they were added at only 2.5 μg/ml. Statistical analysis over all concentrations tested indicated that laidlomycin phenylcarbamate was superior to laidlomycin ($P<0.05$) for inhibiting lactic acid production.

TABLE 1

| COMPOSITION OF BUFFERS USED | | |
|---|---|---|
| Constituent | VFA fermentation mmol/liter | Lactic acid fermentation mmol/liter |
| $NaHCO_3$ | 117.0 | |
| $Na_2HPO_4$ | 26.0 | 20.0 |
| $NaH_2PO_4$ | | 60.0 |
| NaCl | 7.4 | 7.4 |
| KCl | 5.8 | 5.8 |
| $CaCl_2$ | .5 | .5 |
| $MgSO_4.7H_2O$ | .5 | .5 |
| $K_2SO_4$ | .9 | .9 |
| Glucose | 6.0 | 150.0 |
| Maltose[a] | 14.0 | |
| Cellobiose[a] | 24.0 | |
| Soluble starch[a] | 36.0 | |
| Trypticase[b] | 2.5 | 1.5 |
| Urea | 2.0 | 5.0 |

[a]Values are hexose equivalents.
[b]g/liter.

TABLE 2

| PROPIONIC ACID PRODUCTION RATES | | |
|---|---|---|
| Concentration of Compound (μg/ml) | Laidlomycin | Laidlomycin phenylcarbamate (mal/ml) |
| 0 | 21.2 (100) | 21.2 (100) |
| 0.31 | 21.1 ( 99) | 22.8 (107) |
| 0.62 | 20.9 ( 98) | 23.4 (110) |
| 1.25 | 20.9 ( 98) | 25.2 (118) |

TABLE 2-continued
PROPIONIC ACID PRODUCTION RATES

| Concentration of Compound (μg/ml) | Laidlomycin (mal/ml) | Laidlomycin phenylcarbamate (mal/ml) |
|---|---|---|
| 2.50 | 21.8 (102) | 25.7 (121) |
| 5.00 | 22.2 (104) | 26.9 (126) |
| 10.00 | 23.1 (108) | 27.0 (127) |
| 20.00 | 23.2 (109) | 28.2 (133) |

Numbers in parentheses are percentages of control.

TABLE 3
LACTIC ACID PRODUCTION RATES

| Concentration of Compound (μg/ml) | Laidlomycin (mal/ml) | Laidlomycin phenylcarbamate (mal/ml) |
|---|---|---|
| 0 | 27.8 (100) | 27.8 (100) |
| 0.31 | 28.3 (101) | 28.4 (102) |
| 0.62 | 30.7 (110) | 27.7 ( 99) |
| 1.25 | 26.4 ( 94) | 15.6 ( 56) |
| 2.50 | 32.0 (115) | 6.1 ( 21) |
| 5.00 | 26.5 ( 95) | 3.8 ( 13) |
| 10.00 | 21.6 ( 77) | 4.0 ( 14) |
| 20.00 | 22.7 ( 81) | 3.8 ( 13) |

Numbers in parentheses are percentages of control.

EXAMPLE 3
Anticoccidial Activity

Broiler chicks were reared, 12 per cage, in wire-floored battery cages under conditions which prevented extraneous coccidial infections. All chicks received a nonmedicated starter diet ad libitum until 8 days of age. From 8 days of age until the end of the study, chicks received the test diets which contained either O, 99, 121, 143 or 165 ppm of laidlomycin phenylcarbamate per kg of feed. Three replicate pens per treatment were used for all levels of experimental compounds tested.

At 10 days of age, birds were orally challenged with 200,000 oocycts of the coccidia, *Eimeria acervulina,* and 20,000 oocysts of *Eimeria maxima* per bird. The birds were weighed immediately preceding the coccidial challenge and again 7 days later. At 7 days following coccidial challenge, all birds were killed and lesions in the upper and middle sections of the intestinal tracts of six preselected birds per cage were scored on a scale of 0 to 4 based upon their number and severity. Feed present at the time of coccidial challenge and remaining 7 days later was used to determine the effects of compounds upon total feed consumption and feed efficiency.

Results of this assay, illustrated in the accompanying Table 1, clearly demonstrate that protection against coccidiosis was afforded by all non-zero concentrations of laidlomycin phenylcarbamate tested. Laidlomycin phenylcarbamate doubled weight gain, halved the quantity of feed required per unit of gain, and greatly reduced lesion scores in the upper and middle intestines.

TABLE 4
EFFICACY OF LAIDLOMYCIN PHENYLCARBAMATE AS AN ANTICOCCIDIAL AGENT FOR CHICKS

| Variable | Concentration of laidlomycin phenylcarbamate (mg/kg of feed) | | | | |
|---|---|---|---|---|---|
| | 0 | 99 | 121 | 143 | 165 |
| Starting weight, kg[a] | 2.32 | 2.32 | 2.25 | 2.39 | 2.32 |
| Final weight, kg | 3.04 | 3.86 | 3.72 | 3.97 | 4.21 |
| Gain, kg/7 d | .72 | 1.54 | 1.47 | 1.58 | 1.89 |
| Feed consumption, kg/7 d | 3.00 | 3.40 | 3.19 | 3.46 | 3.47 |
| Feed efficiency, feed/gain | 4.18 | 2.21 | 2.16 | 2.19 | 1.84 |
| Lesion scores[b] | | | | | |
| upper intestine | 2.83 | 1.20 | 1.23 | 0.50 | 0.66 |
| middle intestine | 2.87 | 1.43 | 1.57 | 1.47 | 0.70 |

[a]Experimental unit was the cage containing 12 chicks.
[b]Scores are on a scale of 0 to 4 which range from least to most severe.

EXAMPLE 4

Laidlomycin phenylcarbamate, laidlomycin isopopylcarbamate and two laidlomycin esters were prepared and their relative stability at 60° C. methanol-water, acetate buffer was determined. A complete list of the esters and carbamates which were tested under these conditions follows:

| Laidlomycin Derivatives | $t_{\frac{1}{2}}$(hours) |
|---|---|
| propionate | 11.1 |
| butyrate | 22.3 |
| isopropylcarbamate | 501.8 |
| phenylcarbamate | 784 |

EXAMPLE 5

Stability of laidlomycin esters and phenyl carbamate in Soybean Millrun Premix Formulation Two laidlomycin esters and the phenyl carbamate were formulated into a standard soybean meal feed premix. These materials were then stored at 60° C. and analyzed for starting material at one week. The premix composition is given in Table 5 and the stability data in Table 6.

TABLE 5
PREMIX COMPOSITION

| Laidlomycin derivative | 10% (w/w) |
|---|---|
| Ethoxyquin | 0.05% |
| Mineral oil | 3% |
| Soybean mill run q.s. to | 100% |

TABLE 6

| Compound | % Remaining at one week, 60° C. |
|---|---|
| Laidlomycin propionate | 59 |
| Laidlomycin isobutyrate | 70 |
| Laidlomycin phenyl carbamate | 100 |

What is claimed is
1. A compound of the formula

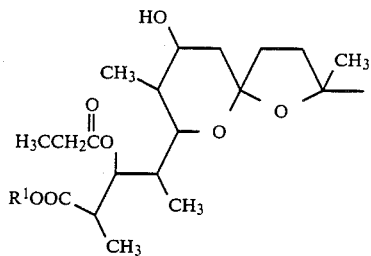

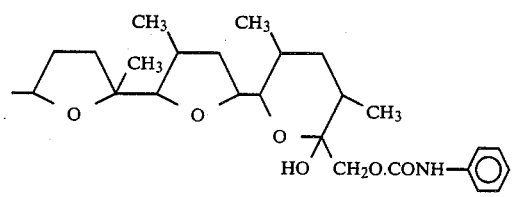

wherein $R^1$ is an alkali metal cation or hydrogen.

2. A compound of claim 1 wherein $R^1$ is hydrogen, sodium or potassium.

3. A compound of claim 2 wherein $R^1$ is hydrogen, i.e., laidlomycin phenyl carbamate.

4. A method of increasing the efficiency of food utilization in a ruminant animal having a developed rumen function which comprises the oral administration to such animal of a propionate-increasing amount of a compound of claim 1.

5. The method of claim 4 wherein $R^1$ is hydrogen.

6. A veterinary pharmaceutical composition which comprises a compound of claim 1 in combination with a suitable feed carrier wherein said compound is present in an amount sufficient to provide a daily dose of between 0.1 to 3.0 mg/kg/body weight.

7. A feed premix for medicating feed which comprises 1 to 400 g of a compound according to claim 1 per pound of premix.

* * * * *